United States Patent [19]

Reich et al.

[11] Patent Number: 5,345,821
[45] Date of Patent: Sep. 13, 1994

[54] RELATIVE HUMIDITY SENSING APPARATUS

[75] Inventors: William L. Reich; David B. Call, both of Boulder, Colo.

[73] Assignee: A.I.R., Inc., Boulder, Colo.

[21] Appl. No.: 5,015

[22] Filed: Jan. 15, 1993

[51] Int. Cl.$^5$ .................. G01N 27/22; G01N 33/18
[52] U.S. Cl. .................. 73/335.04; 324/664; 422/98
[58] Field of Search ............ 73/29.02, 335.02, 335.03, 73/335.04; 324/664, 689, 694; 361/286, 313; 340/602; 422/98; 204/430, 153.22

[56] References Cited

U.S. PATENT DOCUMENTS

| | | | |
|---|---|---|---|
| 3,168,829 | 2/1965 | Nelson | 73/335.04 |
| 3,350,941 | 11/1967 | Misevich et al. | 73/335.04 |
| 3,802,268 | 4/1974 | Thoma | 73/335.04 |
| 4,164,868 | 8/1979 | Suntola | 73/335.04 |
| 4,345,301 | 8/1982 | Nelson | 73/335.04 X |
| 4,562,725 | 1/1986 | Oka et al. | 73/335.02 X |
| 4,893,214 | 1/1990 | Nishiwaki et al. | 361/286 |
| 4,924,172 | 5/1990 | Holmgren | 324/664 |
| 5,036,704 | 8/1991 | Pusatcioglu et al. | 73/335.02 |
| 5,050,434 | 9/1991 | Demisch | 361/286 X |
| 5,161,085 | 11/1992 | Sakai et al. | 361/286 |

Primary Examiner—Robert J. Warden
Assistant Examiner—Robert Carpenter
Attorney, Agent, or Firm—John E. Reilly

[57] ABSTRACT

A relative humidity sensor includes a printed circuit board having a central passageway therethrough and a dielectric film extending across the passageway with electrodes mounted on that portion of the film in the passageway so as to generate a capacitance which will vary directly with the amount of moisture content in the film.

17 Claims, 1 Drawing Sheet

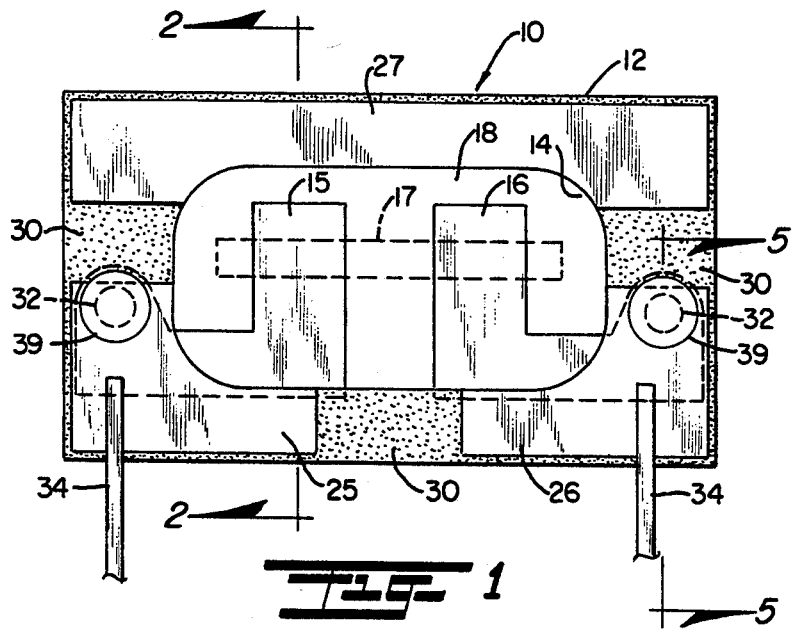
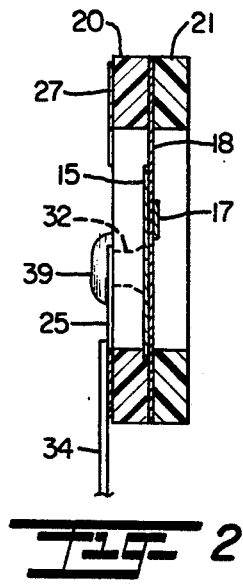
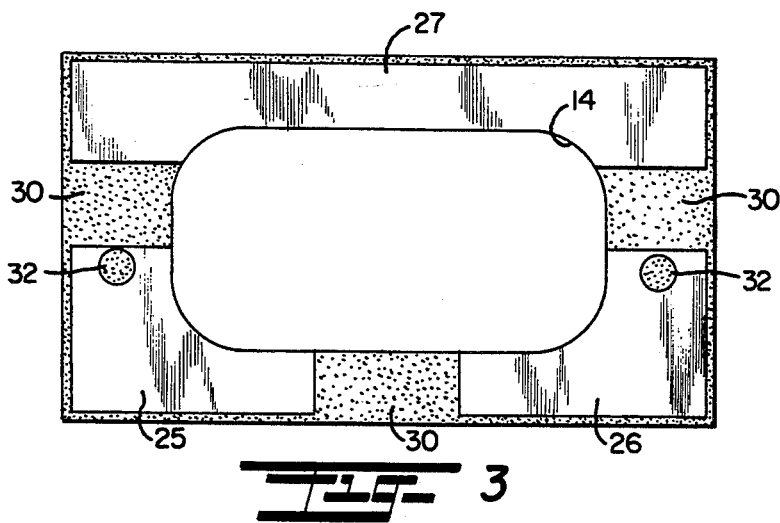
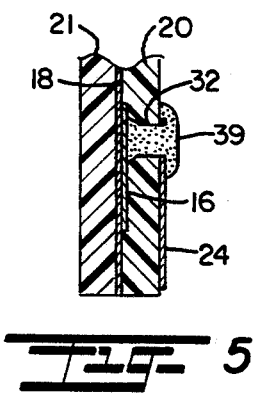
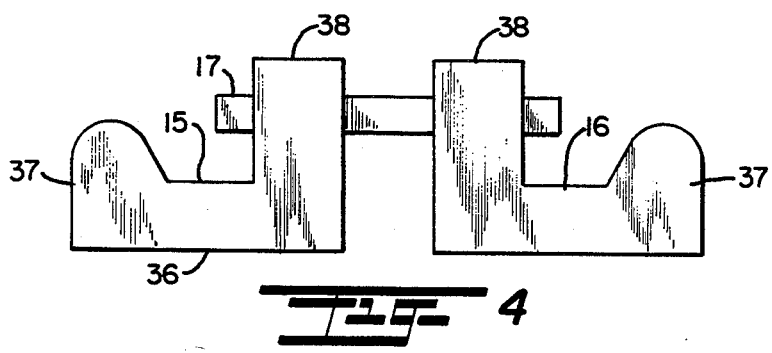

RELATIVE HUMIDITY SENSING APPARATUS

This invention relates to humidity sensing devices; and more particularly relates to a novel and improved thin membrane capacitive sensing device for measuring relative humidity in the air.

BACKGROUND AND FIELD OF INVENTION

It is customary to employ a water permeable film as a dielectric coated on opposite surfaces with electrodes whereby variations in capacitance across the electrodes is proportional to the moisture content in the space or air in contact with the film. In the past, the film has been mounted on a solid substrate so as not to be fully exposed to the surrounding air, or at least is exposed only on one side, and it has been found that the substrate upon which the film is mounted has a thermal mass which affects the accuracy of measurement and slows the response time of the sensor. Representative capacitive sensing devices are those set forth and described in prior U.S. Pat. Nos. 3,350,941 to K. W. Misevich e al; 3,168,829 to D. E. Nelson and 4,164,868 to T. S. Suntola.

It is therefore desirable to provide a humidity sensing device in which the dielectric film and capacitive electrodes are so mounted and arranged as to be fully exposed to air on opposite surfaces of the film supporting the electrodes; yet, the dielectric film is sufficiently thin as to greatly reduce the response time and increase the sensitivity of the device for measurement purposes. In this regard, it is important to avoid a thermal time constant and to make possible the measurement of high frequency fluctuations in the diffusion of humidity. In other words, in the atmosphere, the humidity is not homogenous and it is therefore important to be able to measure even slight fluctuations or variations in humidity diffusion with respect to time.

SUMMARY OF INVENTION

It is therefore an object of the present invention to provide for a novel and improved relative humidity sensor which avoids thermal time constants and reduces the response time in measuring the moisture content in the air.

It is another object of the present invention to provide in a relative humidity sensor for the novel and improved mounting and disposition of a capacitor on a dielectric film so as to be freely exposed to the moisture content in the air on both sides of the film but is capable of withstanding movement of air and other media against the film.

It is a further object of the present invention to provide a relative humidity sensor which is compact, high strength and is readily conformable for use in various airborne or ground applications in measuring changes in humidity with a minimum of response time required; and further wherein the sensor is capable of measuring high frequency fluctuations in the diffusion of humidity.

In a humidity sensor in accordance with the present invention, a support member has a central passageway, a film of material extending across the passageway including means for securing the film to the support member in outer surrounding relation to the passageway and electrode members disposed on the film including capacitive electrode portions in overlapping relation to one another with said film interposed therebetween to define a capacitor between the electrode portions, the film being water permeable and having a dielectric constant which varies directly with the amount of moisture absorbed into the film, and means establishing electrical contact between the electrodes and the electrically conductive portions on the support member.

Preferably, the film is anchored between laminated layers of the support member and is on the order of 0.5 microns to 2 microns so as to be highly sensitive and rapidly respond to changes in moisture content in the surrounding air. The passageway is sized to encourage maximum exposure of the film to the surrounding air, and the electrode members are in direct electrical contact with conduits extending from the intermediate surface to the spaced electrically conductive portions on an external surface of the support member.

The above and other objects of the present invention will become more readily appreciated and understood from a consideration of the following detailed description of a preferred form of invention when taken together with the accompanying drawings in which:

BRIEF DESCRIPTION OF THE DRAWINGS

FIG. 1 is an elevational view of the preferred form of sensing device in accordance with the present invention;

FIG. 2 is a cross-sectional view taken about lines 2—2 of FIG. 1;

FIG. 3 is a plan view of the exposed support surface for the dielectric film;

FIG. 4 is a view in detail of a multi-element electrode pattern employed in the preferred form of invention; and FIG. 5 is an enlarged view in section of the electrodes and dielectric film in accordance with the present invention.

DETAILED DESCRIPTION OF PREFERRED EMBODIMENT

Referring in detail to the drawings, there is illustrated in FIGS. 1 to 4 a preferred form of humidity sensing device 10 which is broadly comprised of a support member in the form of a printed circuit board 12 having a central cut-out area defining a passageway 14 through the printed circuit board 12. A plurality of electrodes 15, 16 and 17 are formed by metal deposition on opposite sides of a dielectric film member 18 which is sandwiched between layers 20 and 21 of the board 12 with the electrodes disposed on the exposed portion of the film 18 extending across the cut-out area 14. On the front or outer surface of the board 12, a conductive surface layer 24 is etched as designated by areas 30 to define the spaced conductive surface portions 25 and 26 as well as an upper surface portion 27 which is left to maintain a uniform thickness in the layer across the dimension of the board and to strengthen the board 12. Plated holes 32 extend through the thickness of the layer 20 of the circuit board 12 to establish electrical connection from the electrodes 15 and 16 into the conductive surface portions 25 and 26 and conductive wires 34, the latter being affixed to the front surface of the board 12 to complete connection into a conventional sensing circuit, such as, a bridge circuit capable of measuring variations in capacitance across the electrodes 15, 16 and 17.

An important feature of the present invention resides in the mounting and disposition of the dielectric film 18 across the cut-out area or passageway 14 with that portion of the film supporting the capacitive portions of the electrodes 15 to 17 fully exposed on both sides to the movement of air through the cut-out area 14. In the preferred form, the dielectric film 18 is composed of a water permeable plastic material having a dielectric constant which varies directly with the amount of moisture therein, such as, cellulose acetate butyrate having a thickness in the range of 0.5 microns to 2 microns. The film 18 is dimensioned to correspond to the rectangular dimension of the board 12. The electrodes 15 and 16 are of generally U-shaped configuration, each having a lower closed end 36, outside, relatively short vertical legs 37 and inside relatively long vertical legs 38. The electrodes 15 and 16 are disposed on one side of the film 18 nearest to the layer 20 so that the outside legs 37 are disposed in direct electrical contact with the plated holes 32; and the inside legs 38 are disposed in closely spaced, parallel relation to one another intermediately of the cut-out area 14. The electrode 17 is disposed on the opposite side of the film 18 to the electrodes 15 and 16 and is in the form of a narrow elongated strip of metal extending transversely to the legs 38 and overlapping the upper free ends of the legs 38 so as to define a pair of spaced capacitors at the intersecting areas of the electrodes 17 and the inner legs 38. Preferably the film 18 is less than 1 micron in thickness and the electrodes 15 to 17 are composed of a 500 angstrom gold material vacuum-deposited onto the film.

The cut-out area 14 is generally oval shaped and extends centrally through the entire thickness of the printed circuit board so as to occupy approximately one-third of the area of the printed circuit board 12. The layers 20 and 21 of the board 12 are suitably composed of a non-conductive but high strength rigid material and are laminated together with the film 18 sandwiched therebetween so as to firmly anchor the film between the layers 20 and 21 in surrounding relation to the cut-out area. The layers of the board 12 as described may be laminated together employing conventional bonding techniques; and the conductive wires or legs 34 are permanently attached to the front surface of the board 12. Preferably, the plated holes 32 are filled with a conductive epoxy material 39 so that, as shown in FIG. 5, electrical connection is completed between the electrodes 15 and 16 via conductive surface portions 25 and 26 into the legs 34.

The sensor of the present invention is particularly adaptable for use in airborne weather instruments, such as, those employed in atmospheric research but is also conformable for use in other ground and aircraft applications and may either be moving or stationary in taking measurements. Although a dual capacitor has been described, it will be apparent that either a single element or multi-element capacitor in series or in parallel may be mounted on the film to extend across the passageway 14 as described. By supporting the film 360° around the sensing area, it is possible to support dielectric films of less than 1 micron thick with enough strength to withstand the rigors of moving air or other moving forces; and at the same time the air and moisture content in the air will freely contact both sides of the dielectric film so as to increase the sensitivity and decrease the response time of the sensor while removing any effect of thermal mass of the substrate from the sensor. In general, the larger the area of overlap between the electrodes, the larger the capacitance value; also, the thinner the dielectric film 18, the larger the capacitance value and the faster the response time of the sensor. In prior art sensors, the dielectric film or support was thick enough that it was necessary for a molecule of water to travel the full distance through the dielectric; instead, by designing the dielectric to be of less than 2 microns in thickness and supporting in the manner described, it is necessary only for the molecule to travel one-half the thickness of the film in order to be sensed. Again, this design avoids a thermal time constant and greatly reduces the response time of the sensor to a period as low as 0.1 seconds. Moreover, it is possible to measure high frequency fluctuations in the diffusion of humidity; i.e., in the atmosphere, the humidity is not homogenous and it is therefore important to be able to measure rapid fluctations in humidity with respect to time.

It is therefore to be understood that while a preferred form of relative humidity sensor is herein set forth and described, the above and other modifications and changes may be made without departing from the spirit and scope of the present invention as defined by the appended claims and reasonable equivalents thereof.

We claim:

1. A humidity sensor comprising a support member having a substantially flat support surface and a passageway extending completely through said support member in a direction normal to said surface, said passageway being entirely surrounded by said support member;

a pair of electrically conductive portions on said support member;

a film of material traversing said passageway including means for securing said film to said support member; and electrode members disposed on said film including at least two capacitive electrode portions with said film interposed therebetween to define a capacitor between said electrode portions, said film being water permeable and having a dielectric constant which varies directly with the amount of moisture therein, and means for establishing electrical contact between said electrically conductive portions.

2. A humidity sensor according to claim 1 wherein said capacitive electrode portions are disposed on said film so as to be exposed to air flow through said passageway.

3. A humidity sensor according to claim 2 wherein said capacitive electrode portions are disposed symmetrically between edges of said support members surrounding said passageway.

4. A humidity sensor according to claim 1 wherein said film has a thickness on the order of 0.05 microns to 2 microns.

5. A humidity sensor according to claim 1 wherein said support member includes layers of electrically non-conductive material, and said surface portion includes spaced electrically conductive coatings defining said pair of electrically conductive portions on said support member.

6. A humidity sensor according to claim 1 wherein said electrodes comprise gold coatings applied to said film.

7. A humidity sensor according to claim 1 wherein said support member is in the form of a planar printed circuit board consisting of layers of electrically non-conductive material, said film disposed between said layers, and said passageway extending through said printed circuit board in a direction normal to said layers.

8. A humidity sensor according to claim 7 wherein each of said electrode members has said conductive portions in the form of leg members extending away from said passageway over said film, and each of said capacitive electrode portions being elongated portions.

9. A humidity sensor according claim 1 wherein said electrode members includes a pair of spaced electrodes on one surface of said film having spaced capacitive electrode portions, and a third capacitive electrode portion disposed on an opposite surface of said film and at least partially overlapping areas on said pair of said capacitive electrode portions.

10. A humidity sensor according to claim 9 wherein said support member is in the form of a printed circuit board comprised of layers of electrically non-conductive material, an intermediate layer defining said support surface and said pair of spaced electrically conductive portions disposed on an external surface of said board, and electrically conductive terminals extending from each of spaced electrodes through said layers to external surface of said printed circuit board.

11. A humidity sensor according to claim 10 wherein said terminals are disposed on opposite sides of said passageway and being in the form of electrically plated holes.

12. A humidity sensor comprising a support member having a substantially flat support surface and a central passageway extending completely through said support member in a direction normal to said surface:
- a film of material traversing said passageway including means for anchoring said film between said layers; and
- electrode members disposed on said film so as to be exposed to air flowing through said passageway including capacitive electrode portions with said film interposed therebetween to define a capacitor between said electrode portions, said film being water permeable and having a dielectric constant which varies directly with the amount of moisture therein, and means for electrically connecting said electrode members to said electrically conductive portions.

13. A humidity sensor according to claim 12 wherein said capacitive electrode portions are disposed symmetrically between edges of said support members surrounding said passageway.

14. A humidity sensor according to claim 1 wherein said film has a thickness on the order of 0.05 microns to 2 microns.

15. A humidity sensor according to claim 12 wherein said support member is in the form of a planar printed circuit board consisting of layers of electrically non-conductive material, and said passageway extending through said printed circuit board in a direction normal to said layers.

16. A humidity sensor according to claim 15 wherein each of said electrode members has said conductive portions in the form of wide leg members extending away from said passageway over said support surface, and each of said capacitive electrode portions being narrow elongated portions.

17. A humidity sensor according to claim 12 wherein said electrode members includes at least one electrode on one surface of said film, and a second capacitive electrode portion disposed on an opposite surface of said film in partially overlapping relation to said one electrode portion.

* * * * *